US008969246B2

(12) United States Patent
Langewald et al.

(10) Patent No.: US 8,969,246 B2
(45) Date of Patent: Mar. 3, 2015

(54) PESTICIDAL MIXTURES

(71) Applicant: BASF SE, Ludwigshafen (DE)

(72) Inventors: Jürgen Langewald, Mannheim (DE); Reinhard Stierl, Kaohsiung County (TW)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/800,292

(22) Filed: Mar. 13, 2013

(65) Prior Publication Data

US 2013/0267414 A1 Oct. 10, 2013

Related U.S. Application Data

(63) Continuation of application No. 12/441,405, filed as application No. PCT/EP2007/059758 on Sep. 17, 2007, now Pat. No. 8,420,569.

(60) Provisional application No. 60/845,382, filed on Sep. 18, 2006, provisional application No. 60/885,273, filed on Jan. 17, 2007.

(51) Int. Cl.
*A01N 43/56* (2006.01)
*A01N 43/90* (2006.01)
*A01P 3/00* (2006.01)
*A01P 5/00* (2006.01)
*A01P 7/02* (2006.01)
*A01P 7/04* (2006.01)

(52) U.S. Cl.
CPC ............... *A01N 43/56* (2013.01); *A01N 43/90* (2013.01)
USPC ....... 504/100; 514/259.31; 514/341; 514/406

(58) Field of Classification Search
USPC ...................... 504/100; 514/259.31, 341, 406
See application file for complete search history.

(56) References Cited

U.S. PATENT DOCUMENTS

| | | | |
|---|---|---|---|
| 2,791,605 A | 5/1957 | Dorman et al. | |
| 3,499,086 A | 3/1970 | Brueckner et al. | |
| 4,139,616 A | 2/1979 | Ducret et al. | |
| 4,567,263 A | 1/1986 | Eicken et al. | |
| 4,617,303 A | 10/1986 | Eicken et al. | |
| 4,914,128 A | 4/1990 | Schirmer et al. | |
| 7,232,836 B2* | 6/2007 | Lahm et al. | 514/341 |
| 7,875,634 B2* | 1/2011 | Hughes et al. | 514/341 |
| 2002/0091067 A1 | 7/2002 | Assmann et al. | |
| 2005/0143428 A1 | 6/2005 | Dunkel et al. | |
| 2005/0261314 A1 | 11/2005 | i Blasco et al. | |
| 2007/0060579 A1 | 3/2007 | Wachendorff-Neumann et al. | |
| 2007/0167463 A1 | 7/2007 | Blasco et al. | |
| 2007/0173408 A1 | 7/2007 | Blasco et al. | |
| 2007/0179061 A1 | 8/2007 | Blasco et al. | |
| 2007/0232598 A1 | 10/2007 | Funke et al. | |
| 2008/0027114 A1 | 1/2008 | Funke et al. | |
| 2008/0070863 A1 | 3/2008 | Funke et al. | |
| 2008/0108686 A1 | 5/2008 | Gewehr et al. | |
| 2008/0139581 A1 | 6/2008 | Grammenos et al. | |
| 2008/0262000 A1 | 10/2008 | Schafer et al. | |

FOREIGN PATENT DOCUMENTS

| | | |
|---|---|---|
| CA | 2597022 | 8/2006 |
| EP | 71792 | 2/1983 |
| EP | 141317 | 5/1985 |
| EP | 226917 | 7/1987 |
| EP | 1028125 | 8/2000 |
| EP | 1035122 | 9/2000 |

(Continued)

OTHER PUBLICATIONS

International Search Report and Written Opinion of the International Searching Authority for International Application No. PCT/EP2007/059758; International Filing Date: Sep. 17, 2007; Date of Completion: Oct. 16, 2008; Date of Mailing: Nov. 6, 2008.

International Preliminary Report on Patentability for International Application No. PCT/EP2007/059758; International Filing Date: Sep. 17, 2007; Date of Issuance: Mar. 24, 2009.

*Primary Examiner* — John Pak

(74) *Attorney, Agent, or Firm* — Brinks Gilson & Lione

(57) ABSTRACT

Pesticidal mixtures comprising, as active components, 1) an anthranilamid compound of the formula I

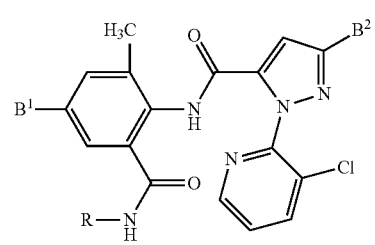

wherein the variables are defined according to the description, and 2) at least one fungicidal compound II selected from the following groups:

strobilurins, carboxamides, heterocylic compounds and other active compounds according to the description, in a synergistically effective amount, methods for controlling pests, and harmful fungi, methods of protecting plants from attack or infestation by insects, acarids or nematodes, methods for treating, controlling, preventing or protecting an animal against infestation or infection by parasites, compositions containing these mixtures, and methods for their preparation.

14 Claims, No Drawings

(56) References Cited

FOREIGN PATENT DOCUMENTS

| | | |
|---|---|---|
| EP | 1201648 | 5/2002 |
| FR | 2254276 | 7/1975 |
| GB | 857383 | 12/1960 |
| WO | WO 98/46608 | 10/1998 |
| WO | WO 99/24413 | 5/1999 |
| WO | WO 0142223 | 6/2001 |
| WO | WO 03009687 | 2/2003 |
| WO | WO 03014103 | 2/2003 |
| WO | WO 03015518 | 2/2003 |
| WO | WO 03024222 | 3/2003 |
| WO | WO 03053145 | 7/2003 |
| WO | WO 03066609 | 8/2003 |
| WO | WO 2004033468 | 4/2004 |
| WO | WO 2004046129 | 6/2004 |
| WO | WO 2004049804 | 6/2004 |
| WO | WO 2004067528 | 8/2004 |
| WO | WO 2005034628 | 4/2005 |
| WO | WO 2005048711 | 6/2005 |
| WO | WO 2005048712 | 6/2005 |
| WO | WO 2005048713 | 6/2005 |
| WO | WO 2005087771 | 9/2005 |
| WO | WO 2005087772 | 9/2005 |
| WO | WO 2005087773 | 9/2005 |
| WO | WO 2005123689 | 12/2005 |
| WO | WO 2005123690 | 12/2005 |
| WO | WO 2006055922 | 5/2006 |
| WO | WO 2006087325 | 8/2006 |
| WO | WO 2006087343 | 8/2006 |
| WO | WO 2006092428 | 9/2006 |
| WO | WO 2006108552 | 10/2006 |
| WO | WO 2006120219 | 11/2006 |
| WO | WO 2007017450 | 2/2007 |

* cited by examiner

PESTICIDAL MIXTURES

This application is a Continuation application of U.S. patent application Ser. No. 12/441,405, filed Mar. 16, 2009, the entire contents of which is hereby incorporated herein by reference. U.S. patent application Ser. No. 12/441,405 is a National Stage application of International Application No. PCT/EP2007/059758, filed Sep. 17, 2007, which claims the benefit of U.S. Provisional Application No. 60/845,382, filed Sep. 18, 2006, and U.S. Provisional Application No. 60/885,273, filed Jan. 17, 2007, the entire contents of which is hereby incorporated herein by reference

DESCRIPTION

The present invention relates to pesticidal mixtures comprising, as active components,
1) an anthranilamide compound of formula I

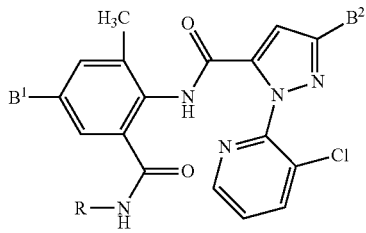

in which the substituents are as defined below:
$B^1$ is hydrogen, cyano or chlorine;
$B^2$ is bromine or $CF_3$; and
R is hydrogen or $C_1$-$C_6$-alkyl;
and
2) at least one fungicidal compound II selected from the following groups:
   A) strobilurins, selected from: methyl (2-chloro-5-[1-(3-methylbenzyloxy-imino)ethyl]benzyl)carbamate, methyl (2-chloro-5-[1-(6-methylpyridin-2-yl-methoxy-imino)ethyl]benzyl)carbamate and methyl 2-(ortho-((2,5-dimethyl-phenyloxymethylene)phenyl)-3-methoxy-acrylate;
   B) carboxamides, selected from: furametpyr, tiadinil, N-(4'-bromobiphenyl-2-yl)-4-difluoromethyl-2-methylthiazole-5-carboxamide, N-(4'-trifluoromethylbiphenyl-2-yl)-4-difluoromethyl-2-methylthiazole-5-carboxamide, N-(4'-chloro-3'-fluorobiphenyl-2-yl)-4-difluoromethyl-2-methylthiazole-5-carboxamide, N-(3',4'-dichloro-4-fluorobiphenyl-2-yl)-3-difluoromethyl-1-methylpyrazole-4-carboxamide, N-(3',4'-dichloro-5-fluorobiphenyl-2-yl)-3-difluoromethyl-1-methylpyrazole-4-carboxamide; 3,4-dichloro-N-(2-cyanophenyl)isothiazol-5-carboxamide; N-(2',4'-difluorobiphenyl-2-yl)-1-methyl-3-trifluoromethyl-1H-pyrazole-4-carboxamide; N-(2',4'-dichlorobiphenyl-2-yl)-1-methyl-3-trifluoromethyl-1H-pyrazole-4-carboxamide; N-(2',4'-difluorobiphenyl-2-yl)-3-difluoromethyl-1-methyl-1H-pyrazole-4-carboxamide; N-(2',4'-dichlorobiphenyl-2-yl)-3-difluoromethyl-1-methyl-1H-pyrazole-4-carboxamide; N-(2',5'-difluorobiphenyl-2-yl)-1-methyl-3-trifluoromethyl-1H-pyrazole-4-carboxamide; N-(2',5'-dichlorobiphenyl-2-yl)-1-methyl-3-trifluoromethyl-1H-pyrazole-4-carboxamide; N-(2',5'-difluorobiphenyl-2-yl)-3-difluoromethyl-1-methyl-1H-pyrazole-4-carboxamide; N-(2',5'-dichlorobiphenyl-2-yl)-3-difluoromethyl-1-methyl-1H-pyrazole-4-carboxamide; N-(3',5'-difluorobiphenyl-2-yl)-1-methyl-3-trifluoromethyl-1H-pyrazole-4-carboxamide; N-(3',5'-dichlorobiphenyl-2-yl)-1-methyl-3-trifluoromethyl-1H-pyrazole-4-carboxamide, N-(3',5'-difluorobiphenyl-2-yl)-3-difluoromethyl-1-methyl-1H-pyrazole-4-carboxamide; N-(3',5'-dichlorobiphenyl-2-yl)-3-difluoromethyl-1-methyl-1H-pyrazole-4-carboxamide; N-(3'-fluorobiphenyl-2-yl)-1-methyl-3-trifluoro-methyl-1H-pyrazole-4-carboxamide, N-(3'-chlorobiphenyl-2-yl)-1-methyl-3-trifluoromethyl-1H-pyrazole-4-carboxamide; N-(3'-fluorobiphenyl-2-yl)-3-difluoromethyl-1-methyl-1H-pyrazole-4-carboxamide, N-(3'-chlorobiphenyl-2-yl)-3-difluoromethyl-1-methyl-1H-pyrazole-4-carbox-amide; N-(2'-fluoro-biphenyl-2-yl)-1-methyl-3-trifluoromethyl-1H-pyrazole-4-carboxamide; N-(2'-chlorobiphenyl-2-yl)-1-methyl-3-trifluoromethyl-1H-pyrazole-4-carboxamide; N-(2'-fluorobiphenyl-2-yl)-3-difluoromethyl-1-methyl-1H-pyrazole-4-carboxamide; N-(2'-chlorbiphenyl-2-yl)-3-difluoromethyl-1-methyl-1H-pyrazole-4-carboxamide; N-(2'-fluoro-4'-chloro-5'-methyl-biphenyl-2-yl)-1-methyl-3-trifluoromethyl-1H-pyrazole-4-carboxamide; N-(3',4',5'-trifluorobiphenyl-2-yl)-1-methyl-3-trifluoromethyl-1H-pyrazole-4-carboxamide; N-(3',4',5'-trifluorobiphenyl-2-yl)-1-methyl-3-difluoromethyl-1H-pyrazole-4-carboxamide; N-(2',4',5'-trifluorobiphenyl-2-yl)-1-methyl-3-difluoromethyl-1H-pyrazole-4-carboxamide; N-(3',4',5'-trifluorobiphenyl-2-yl)-3-chlorofluoromethyl-1-methyl-1H-pyrazole-4-carboxamide; N-[2-(1,1,2,3,3,3-hexafluoropropoxy)phenyl]-1-methyl-3-trifluoromethyl-1H-pyrazole-4-carboxamide; N-[2-(1,1,2,3,3,3-hexafluoropropoxy)-phenyl]-3-difluoromethyl-1-methyl-1H-pyrazole-4-carboxamide, N-[2-(2-chloro-1,1,2-trifluoroethoxy)phenyl]-1-methyl-3-trifluoromethyl-1H-pyrazole-4-carboxamide; N-[2-(2-chlor-1,1,2-trifluoroethoxy)phenyl]-3-difluoromethyl-1-methyl-1H-pyrazole-4-carboxamide; N-[2-(1,1,2,2-tetrafluoro-ethoxy)phenyl]-3-difluoromethyl-1-methyl-1H-pyrazole-4-carboxamide; N-[2-(1,1,2,2-tetrafluoroethoxy)phenyl]-1-methyl-3-trifluoromethyl-1H-pyrazole-4-carboxamide; N-(4'-(trifluoromethylthio)biphenyl-2-yl)-3-difluoromethyl-1-methyl-1H-pyrazole-4-carboxamide; N-(4'-(trifluoro-methylthio)biphenyl-2-yl)-1-methyl-3-trifluoromethyl-1H-pyrazole-4-carboxamide; 5-fluoro-1,3-dimethyl-1H-pyrazole-4-carboxylic acid [2-(1,2-dimethyl-propyl)-phenyl]-amide, flumetover, carpropamid, and; N-(2-{4-[3-(4-chlorophenyl)prop-2-ynyloxy]-3-methoxyphenyl}ethyl)-2-methanesulfonylamino-3-methylbutyramide, N-(2-{4-[3-(4-chlorophenyl)-prop-2-ynyloxy]-3-methoxyphenyl}ethyl)-2-ethanesulfonylamino-3-methyl-butyramide;
   C) heterocylic compounds, selected from: aldimorph, focthilinone, amisulbrom, diclomezine, 5-chloro-7-(4-methylpiperidin-1-yl)-6-(2,4,6-trifluorophenyl)-[1,2,4]triazolo[1,5-a]pyrimidine, 6-(3,4-di-chlorophenyl)-5-methyl-[1,2,4]triazolo[1,5-a]pyrimidine-7-ylamine, 6-(4-tert-butylphenyl)-5-methyl-[1,2,4]triazolo[1,5-a]pyrimidine-7-ylamine, 5-methyl-6-(3,5,5-trimethylhexyl)-[1,2,4]triazolo[1,5-a]pyrimidine-7-ylamine, 5-methyl-6-octyl-[1,2,4]triazolo[1,5-a]pyrimidine-7-ylamine, 6-methyl-5-octyl-[1,2,4]triazolo[1,5-a]pyrimidine-7-ylamine, 6-ethyl-5-octyl-[1,2,4]triazolo[1,5-a]pyrimidine-7-ylamine, 5-ethyl-6-octyl-[1,2,4]triazolo[1,5-a]pyrimidine-7-ylamine, 5-ethyl-6-(3,5,5- trimethyl-hexyl)-[1,2,4]triazolo[1,5-a]pyrimidine-7-ylamine, 6-octyl-5-propyl-[1,2,4]triazolo[1,5-a]pyrimidine-7-ylamine, 5-methoxymethyl-6-octyl-[1,2,4]triazolo[1,5-a]pyrimidine-7-ylamine, 6-octyl-5-trifluoromethyl-[1,2,4]triazolo[1,5-a]pyrimidine-7-ylamine and 5-trifluoromethyl-6-(3,5,5-trimethyl-hexyl)-[1,2,4]triazolo[1,5-a]pyrimidine-7-ylamine; 2-butoxy-6-iodo-3-propylchromen-4-one; dazomet, 3-[5-(4-chlorophenyl)-2,3-dimethylisoxazolidin-3-yl]pyridine;
and D) other active compounds, selected from metam, methyl 3-(4-chlorophenyl)-3-(2-isopropoxycarbonylamino-3-methylbutyrylamino)propanoate; enilconazole, streptomycin, binapacryl, dinobuton, fentin-acetate, fosetyl, phosphorous acid and its salts, hexachlorobenzene, thiophanate-methyl, and copper acetate;

in a synergistically effective amount.

Moreover, the invention relates to a method for controlling pests, this includes animal pests and harmful fungi, using mixtures of a compound I with active compounds II and to the use of the compounds I with the active compounds II for preparing such mixtures, and also to compositions comprising such mixtures.

In one embodiment the present invention provides methods for the control of insects, acarids or nematodes comprising contacting the insect, acarid or nematode or their food supply, habitat, breeding grounds or their locus with a pesticidally effective amount of mixtures of a compound I with one or more compounds II.

Moreover, in another embodiment the present invention also relates to a method of protecting plants from attack or infestation by insects, acarids or nematodes comprising contacting the plant, or the soil or water in which the plant is growing, with a pesticidally effective amount of a mixture of a compound I with one or more compounds II.

This invention also provides a method for treating, controlling, preventing or protecting an animal against infestation or infection by parasites which comprises orally, topically or parenterally administering or applying to the animals a parasiticidally effective amount of a mixture of a compound I with one or more compounds II.

The invention also provides a process for the preparation of a composition for treating, controlling, preventing or protecting a warm-blooded animal or a fish against infestation or infection by insects, acarids or nematodes which comprises a pesticidally effective amount of a mixture of a compound I with one or more compounds II.

Moreover, the invention relates to a method for controlling harmful fungi using mixtures of a compound I with active compounds II and to the use of a compound I with active compounds II for preparing such mixtures, and also to compositions comprising these mixtures.

The anthranilamide compound of formula I referred to above as component 1, their preparation and their action against insect and acarid pests are known (WO 2004/67528; WO 2004/46129; WO 2004/33468; WO 2003/24222; WO 2003/15518).

Mixtures, active against pests, of compounds of formula I with other insecticides are known in a general manner from WO 2004/67528; WO 2004/46129; WO 2004/33468; WO 2003/24222; WO 2003/15518. WO 2006/055922 discloses anthranilamide derivatives as single compounds, and in mixtures. Binary mixtures of compounds of formula I with other fungicides are described in WO 2006/108552.

The active compounds II mentioned above as component 2, their preparation and their action against harmful fungi are generally known (cf.: http://www.hclrss.demon.co.uk/index.html); they are commercially available. Particularly, they are known from: furametpyr, tiadinil, 3'-chloro-4,4'-dimethyl-1,2,3-thiadiazole-5-carboxanilide [CAS RN 223580-51-6]; flumetover, 2-(3,4-dimethoxyphenyl)-N-ethyl-α,α,α-trifluoro-N-methyl-p-toluamide [AGROW No. 243, 22 (1995)]; carpropamid, 2,2-dichloro-N-[1-(4-chlorophenyl)ethyl]-1-ethyl-3-methylcyclopropanecarboxamide [CAS RN 104030-54-8]; aldimorph, 4-alkyl-2,5 (or 2,6)-dimethylmorpholine, comprising 65-75% of 2,6-dimethylmorpholine and 25-35% of 2,5-dimethylmorpholine, comprising more than 85% of 4-dodecyl-2,5 (or 2,6)-dimethylmorpholine, where "alkyl" may also include octyl, decyl, tetradecyl or hexadecyl and where the cis/trans ratio is 1:1; octhilinone; amisulbrom, N,N-dimethyl-3-(3-bromo-6-fluoro-2-methylindole-1-sulfonyl)-[1,2,4]triazole-1-sulfonamide (WO 03/053145); diclomezine, 6-(3,5-dichlorophenyl)-p-tolyl)pyridazin-3(2H)-one; metam, methyldithiocarbaminic acid (U.S. Pat. No. 2,791,605); streptomycin, O-2-deoxy-2-methylamino-α-L-glucopyranosyl-(1→2)-O-5-deoxy-3-O-formyl-α-L-lyxofuranosyl-(1→4)N1,N3-diamidino-D-streptamine; polyoxins, 5-(2-amino-5-O-carbamoyl-2-deoxy-L-xylonamido)-1-(5-carboxy-1,2,3,4-tetrahydro-2,4-dioxopyrimidin-1-yl)-1,5-dideoxy-β-D-allofuranuronic acid and the salts thereof; binapacryl, (RS)-2-sec-butyl-4,6-dinitrophenyl 3-methylcrotonate; dinobuton, (RS)-2-sec-butyl-4,6-dinitrophenyl isopropyl carbonate; dihydronaphtho[2,3-b][1,4]dithiin-2,3-dicarbonitrile (GB 857 383); fentin acetate, triphenyltin acetate (U.S. Pat. No. 3,499,086); fosetyl, (FR 22 54 276); thiophanate-methyl, 1,2-phenylenebis(iminocarbonothioyl)bis(dimethylcarbamate) (DE-OS 19 30 540).

The compounds named according to IUPAC, their preparation and their fungicidal activity are likewise known: methyl (2-chloro-5-[1-(3-methylbenzyloxyimino)ethyl]benzyl)carbamate, methyl (2-chloro-5-[1-(6-methylpyridin-2-ylmethoxyimino)ethyl]benzyl)carbamate (EP-A 12 01 648); methyl 2-(ortho-((2,5-dimethylphenyloxymethylene)phenyl)-3-methoxyacrylate (EP-A 226 917); 5-chloro-7-(4-methylpiperidin-1-yl)-6-(2,4,6-trifluorophenyl)-[1,2,4]triazolo[1,5-a]pyrimidine (WO 98/46608), 3,4-dichloro-N-(2-cyanophenyl)isothiazole-5-carboxamide (WO 99/24413), N-(2-{4-[3-(4-chlorophenyl)prop-2-ynyloxy]-3-methoxyphenyl}ethyl)-2-methanesulfonylamino-3-methylbutyramide, N-(2-{4-[3-(4-chlorophenyl)prop-2-ynyloxy]-3-methoxyphenyl}ethyl)-2-ethane-sulfonylamino-3-methylbutyramide (WO 2004/049804), N-(4'-bromobiphenyl-2-yl)-4-di-fluoromethyl-2-methylthiazole-5-carboxamide, N-(4'-trifluoromethylbiphenyl-2-yl)-4-difluoromethyl-2-methylthiazole-5-carboxamide, N-(4'-chloro-3'-fluorobiphenyl-2-yl)-4-difluoromethyl-2-methylthiazole-5-carboxamide, N-(3',4'-dichloro-4-fluorobiphenyl-2-yl)-3-difluoromethyl-1-methylpyrazole-4-carboxamide (WO 2003/066609); N-(3',4'-di-chloro-5-fluorobiphenyl-2-yl)-3-difluoromethyl-1-methylpyrazole-4-carboxamide (WO 03/053145); 2-butoxy-6-iodo-3-propylchromen-4-one (WO 2003/14103); 3-[5-(4-chlorophenyl)-2,3-dimethylisoxazolidin-3-yl]pyridine (EP-A 10 35 122); amisulbrom, N,N-dimethyl-3-(3-bromo-6-fluoro-2-methylindole-1-sulfonyl)-[1,2,4]triazole-1-sulfonamide (WO 2003/053145); methyl 3-(4-chlorophenyl)-3-(2-isopropoxycarbonylamino-3-methylbutyrylamino)propanoate (EP-A 1028125); 6-(3,4-dichlorophenyl)-5-methyl-[1,2,4]triazolo[1,5-a]pyrimidine-7-ylamine, 6-(4-tert-butylphenyl)-5-methyl-[1,2,4]triazolo[1,5-a]pyrimidine-7-ylamine, 5-methyl-6-(3,5,5-trimethyl-hexyl)-[1,2,4]triazolo[1,5-a]pyrimidine-7-ylamine, 5-methyl-6-octyl-[1,2,4]triazolo[1,5-a]pyrimidine-7-ylamine, 6-methyl- 5-octyl-[1,2,4]triazolo[1,5-a]pyrimidine-7-ylamine, 6-ethyl-5-octyl-[1,2,4]triazolo[1,5-a]pyrimidine-7-ylamine, 5-ethyl-6-octyl-[1,2,4]triazolo[1,5-a]pyrimidine-7-ylamine, 5-ethyl-6-(3,5,5-trimethyl-hexyl)-[1,2,4]triazolo[1,5-a]pyrimidine-7-ylamine, 6-octyl-5-propyl-[1,2,4]triazolo[1,5-a]pyrimidine-7-ylamine, 5-methoxymethyl-6-octyl-[1,2,4]triazolo[1,5-a]pyrimidine-7-ylamine, 6-octyl-5-trifluoromethyl-[1,2,4]triazolo[1,5-a]pyrimidine-7-ylamine and 5-trifluoromethyl-6-(3,5,5-trimethylhexyl)-[1,2,4]triazolo[1,5-a]pyrimidine-7-ylamine are known from EP-A 71 792; EP-A 141 317; WO 2003/009687; WO 2005/087771; WO 2005/087772; WO 2005/087773; PCT/EP2006/050922; WO 2006/087325 and or WO 2006/092428.

N-(2',4'-difluorobiphenyl-2-yl)-1-methyl-3-trifluoromethyl-1H-pyrazole-4-carboxamide; N-(2',4'-dichlorobiphenyl-2-yl)-1-methyl-3-trifluoromethyl-1H-pyrazole-4-carboxamide; N-(2',4'-difluorobiphenyl-2-yl)-3-difluoromethyl-1-methyl-1H-pyrazole-4-carboxamide; N-(2',4'-dichlorobiphenyl-2-yl)-3-difluoromethyl-1-methyl-1H-pyrazole-4-carboxamide; N-(2',5'-difluorobiphenyl-2-yl)-1-methyl-3-trifluoromethyl-1H-pyrazole-4-carboxamide; N-(2',5'-dichlorobiphenyl-2-yl)-1-methyl-3-trifluoromethyl-1H-pyrazole-4-carboxamide; N-(2',5'-difluorobiphenyl-2-yl)-3-difluoromethyl-1-methyl-1H-pyrazole-4-carboxamide; N-(2',5'-dichlorobiphenyl-2-yl)-3-difluoromethyl-1-methyl-1H-pyrazole-4-carboxamide; N-(3',5'-difluorobiphenyl-2-yl)-1-methyl-3-trifluoromethyl-1H-pyrazole-4-carboxamide; N-(3',5'-dichlorobiphenyl-2-yl)-1-methyl-3-trifluoromethyl-1H-pyrazole-4-carboxamide, N-(3',5'-difluorobiphenyl-2-yl)-3-difluoromethyl-1-methyl-1H-pyrazole-4-carboxamide; N-(3',5'-dichlorobiphenyl-2-yl)-3-difluoromethyl-1-methyl-1H-pyrazole-4-carboxamide; N-(3'-fluorobiphenyl-2-yl)-1-methyl-3-trifluoromethyl-1H-pyrazole-4-carboxamide; N-(3'-chlorobiphenyl-2-yl)-1-methyl-3-trifluoromethyl-1H-pyrazole-4-carboxamide; N-(3'-fluorobiphenyl-2-yl)-3-difluoromethyl-1-methyl-1H-pyrazole-4-carboxamide; N-(3'-chlorobiphenyl-2-yl)-3-difluoromethyl-1-methyl-1H-pyrazole-4-carboxamide; N-(2'-fluorobiphenyl-2-yl)-1-methyl-3-trifluoromethyl-1H-pyrazole-4-carboxamide; N-(2'-chlorobiphenyl-2-yl)-1-methyl-3-trifluoromethyl-1H-pyrazole-4-carboxamide; N-(2'-fluorobiphenyl-2-yl)-3-difluoromethyl-1-methyl-1H-pyrazole-4-carboxamide; N-(2'-chlorbiphenyl-2-yl)-3-difluoromethyl-1-methyl-1H-pyrazole-4-carboxamide; N-(2'-fluoro-4'-chloro-5'-methylbiphenyl-2-yl)-1-methyl-3-trifluoromethyl-1H-pyrazole-4-carboxamide; N-(3',4',5'-trifluorobiphenyl-2-yl)-1-methyl-3-trifluoromethyl-1H-pyrazole-4-carboxamide; N-(3',4',5'-trifluorobiphenyl-2-yl)-1-methyl-3-difluoromethyl-1H-pyrazole-4-carboxamide; N-(2',4',5'-trifluorobiphenyl-2-yl)-1-methyl-3-difluoromethyl-1H-pyrazole-4-carboxamide; N-(3',4',5'-trifluorobiphenyl-2-yl)-3-chlorofluoromethyl-1-methyl-1H-pyrazole-4-carboxamide; N-[2-(1,1,2,3,3,3-hexafluoropropoxy)phenyl]-1-methyl-3-trifluoromethyl-1H-pyrazole-4-carboxamide; N-[2-(1,1,2,3,3,3-hexafluoropropoxy)-phenyl]-3-difluoromethyl-1-methyl-1H-pyrazole-4-carboxamide, N-[2-(2-chloro-1,1,2-trifluoroethoxy)phenyl]-1-methyl-3-trifluoromethyl-1H-pyrazole-4-carboxamide; N-[2-(2-chlor-1,1,2-trifluoroethoxy)phenyl]-3-difluoromethyl-1-methyl-1H-pyrazole-4-carboxamide; 4-carbonsäure-N-[2-(1,1,2,2-tetrafluoroethoxy)phenyl]-3-difluoromethyl-1-methyl-1H-pyrazole-4-carboxamide; N-[2-(1,1,2,2-tetrafluoroethoxy)phenyl]-1-methyl-3-trifluoromethyl-1H-pyrazole-4-carboxamide; N-(4'-(trifluoromethylthio)biphenyl-2-yl)-3-difluoromethyl-1-methyl-1H-pyrazole-4-carboxamide; and N-(4'-(trifluoromethylthio)biphenyl-2-yl)-1-methyl-3-trifluoromethyl-1H-pyrazole-4-carboxamide are known from WO 2006/087343, WO 2001/42223, WO 2005/34628, WO 2005/123689, WO 2005/123690, WO 2006/120219, WO 2007/017450 and/or EP Application No. 06123463.9.

It is an object of the present invention, with a view to reducing the application rates and broadening the activity spectrum of the known compounds, to provide mixtures which, at a reduced total amount of active compounds applied, have improved activity against pests.

One typical problem arising in the field of pest control lies in the need to reduce the dosage rates of the active ingredient in order to reduce or avoid unfavorable environmental or toxicological effects whilst still allowing effective pest control.

In regard to the instant invention the term pests embrace animal pests, and harmful fungi.

Another problem encountered concerns the need to have available pest control agents which are effective against a broad spectrum of pests.

There also exists the need for pest control agents that combine knock-down activity with prolonged control, that is, fast action with long lasting action.

Another difficulty in relation to the use of pesticides is that the repeated and exclusive application of an individual pesticidal compound leads in many cases to a rapid selection of pests, that means animal pests, and harmful fungi, which have developed natural or adapted resistance against the active compound in question. Therefore there is a need for pest control agents that help prevent or overcome resistance.

It was therefore an object of the present invention to provide pesticidal mixtures which solve the problems of reducing the dosage rate and/or enhancing the spectrum of activity and/or combining knock-down activity with prolonged control and/or to resistance management.

We have found that this object is in part or in whole achieved by the combination of active compounds defined at the outset. Moreover, we have found that simultaneous, that is joint or separate, application of a compound I and one or more compounds II or successive application of a compound I and one or more compounds II allows enhanced control of pests, that means animal pests, and harmful fungi, compared to the control rates that are possible with the individual compounds (synergistic mixtures).

In the definitions of the symbols given in formula I, collective terms were used which are generally representative for the following substituents:

alkyl: saturated straight-chain or branched hydrocarbon radicals having 1 to 6, preferably up to 4 carbon atoms, for example $C_1$-$C_4$-alkyl, such as methyl, ethyl, propyl, 1-methylethyl, butyl, 1-methylpropyl, 2-methylpropyl, 1,1-dimethylethyl.

The formula I represents in particular compounds in which R is methyl, ethyl, n-propyl, iso-propyl, n-butyl, sec-butyl, or tert. butyl.

The formula I represents in particular compounds in which $B^1$ is chloro or cyano.

The formula I represents in particular compounds in which $B^2$ is bromo.

One embodiment represents compounds of formula I wherein R is hydrogen. Another embodiment represents compounds of formula I wherein R is $C_1$-$C_4$-alkyl, particularly methyl.

In particular with a view to their use in the mixtures according to the invention, preference is given to the compounds I compiled in the table below.

TABLE I

| No. | $B^1$ | $B^2$ | R |
|---|---|---|---|
| I-1 | H | Br | $CH_3$ |
| I-2 | CN | Br | $CH_3$ |
| I-3 | Cl | Br | $CH_3$ |
| I-4 | H | $CF_3$ | $CH_3$ |
| I-5 | CN | $CF_3$ | $CH_3$ |
| I-6 | Cl | $CF_3$ | $CH_3$ |
| I-7 | H | Br | H |
| I-8 | CN | Br | H |
| I-9 | Cl | Br | H |
| I-10 | H | $CF_3$ | H |
| I-11 | CN | $CF_3$ | H |
| I-12 | Cl | $CF_3$ | H |
| I-13 | H | Br | $CH_2CH_3$ |
| I-14 | CN | Br | $CH_2CH_3$ |
| I-15 | Cl | Br | $CH_2CH_3$ |
| I-16 | H | $CF_3$ | $CH_2CH_3$ |
| I-17 | CN | $CF_3$ | $CH_2CH_3$ |
| I-18 | Cl | $CF_3$ | $CH_2CH_3$ |
| I-19 | H | Br | $CH_2CH_2CH_3$ |
| I-20 | CN | Br | $CH_2CH_2CH_3$ |
| I-21 | Cl | Br | $CH_2CH_2CH_3$ |
| I-22 | H | $CF_3$ | $CH_2CH_2CH_3$ |
| I-23 | CN | $CF_3$ | $CH_2CH_2CH_3$ |
| I-24 | Cl | $CF_3$ | $CH_2CH_2CH_3$ |
| I-25 | H | Br | $CH(CH_3)_2$ |
| I-26 | CN | Br | $CH(CH_3)_2$ |
| I-27 | Cl | Br | $CH(CH_3)_2$ |
| I-28 | H | $CF_3$ | $CH(CH_3)_2$ |
| I-29 | CN | $CF_3$ | $CH(CH_3)_2$ |
| I-30 | Cl | $CF_3$ | $CH(CH_3)_2$ |

Particular preference is given to the combinations of the compounds I-2, or I-3 with any one of the compounds II as defined at the outset. Especially preferred is the compound I-3, 3-bromo-4'-chloro-1-(3-chloro-2-pyridyl)-2'-methyl-6'-(methylcarbamoyl)pyrazole-5-carboxanilide, with the provisional ISO name chlorantraniliprole.

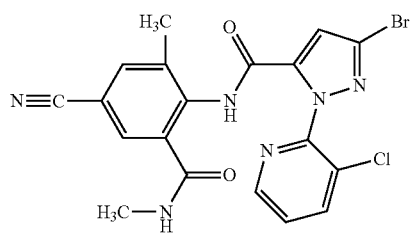

I-2

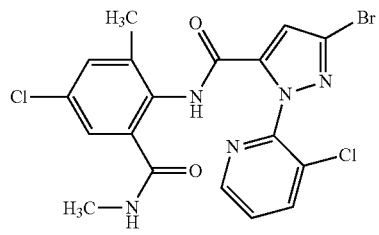

I-3

A preferred embodiment of the invention provides mixtures of a compound I, in particular of any one of compounds I-2, and I-3 with a compound II, which is selected from furametpyr, amisulbrom and diclomezine.

Another preferred embodiment of the invention provides mixtures of carpropamid with any one of the compounds of formula I compiled in table I.

Another preferred embodiment of the invention provides mixtures of furametpyr with any one of the compounds of formula I compiled in table I.

Another preferred embodiment of the invention provides mixtures of thiadinil with any one of the compounds of formula I compiled in table I.

Another preferred embodiment of the invention provides mixtures of N-(3',4'-dichloro-5-fluorobiphenyl-2-yl)-3-difluoromethyl-1-methylpyrazole-4-carboxamide with any one of the compounds of formula I compiled in table I.

Another preferred embodiment of the invention provides mixtures of N-(3',4',5'-trifluoro-biphenyl-2-yl)-1-methyl-3-trifluoromethyl-1H-pyrazole-4-carboxamide with any one of the compounds of formula I compiled in table I.

Another preferred embodiment of the invention provides mixtures of N-(3',4',5'-trifluoro-biphenyl-2-yl)-1-methyl-3-difluoromethyl-1H-pyrazole-4-carboxamide with any one of the compounds of formula I compiled in table I.

Another preferred embodiment of the invention provides mixtures of N-(2',4',5'-trifluoro-biphenyl-2-yl)-1-methyl-3-difluoromethyl-1H-pyrazole-4-carboxamide with any one of the compounds of formula I compiled in table I.

Another preferred embodiment of the invention provides mixtures of N-(3',4',5'-trifluoro-biphenyl-2-yl)-3-chlorofluoromethyl-1-methyl-1H-pyrazole-4-carboxamide with any one of the compounds of formula I compiled in table I.

Another preferred embodiment of the invention provides mixtures of N-[2-(1,1,2,3,3,3-hexafluoropropoxy)phenyl]-1-methyl-3-trifluoromethyl-1H-pyrazole-4-carboxamide with any one of the compounds of formula I compiled in table I.

Another preferred embodiment of the invention provides mixtures of N-[2-(1,1,2,3,3,3-hexafluoropropoxy)-phenyl]-3-difluoromethyl-1-methyl-1H-pyrazole-4-carboxamide with any one of the compounds of formula I compiled in table I.

Another preferred embodiment of the invention provides mixtures of N-[2-(1,1,2,2-tetra-fluoroethoxy)phenyl]-1-methyl-3-trifluoromethyl-1H-pyrazole-4-carboxamide with any one of the compounds of formula I compiled in table I.

Another preferred embodiment of the invention provides mixtures of N-(4'-(trifluoro-methylthio)biphenyl-2-yl)-3-difluoromethyl-1-methyl-1H-pyrazole-4-carboxamide with any one of the compounds of formula I compiled in table I.

Another preferred embodiment of the invention provides mixtures of N-(4'-(trifluoro-methylthio)biphenyl-2-yl)-1-methyl-3-trifluoromethyl-1H-pyrazole-4-carboxamide with any one of the compounds of formula I compiled in table I.

Another preferred embodiment of the invention provides mixtures of 5-fluoro-1,3-di-methyl-1H-pyrazole-4-carboxylic acid [2-(1,2-dimethyl-propyl)-phenyl]-amide, with any one of the compounds of formula I compiled in table I.

Another preferred embodiment of the invention provides mixtures of 5-chloro-7-(4-methylpiperidin-1-yl)-6-(2,4,6-trifluorophenyl)-[1,2,4]triazolo[1,5-a]pyrimidine with any one of the compounds of formula I compiled in table I.

Another preferred embodiment of the invention provides mixtures of 6-(3,4-dichlorophenyl)-5-methyl-[1,2,4]triazolo[1,5-a]pyrimidine-7-ylamine with any one of the compounds of formula I compiled in table I.

Another preferred embodiment of the invention provides mixtures of 6-(4-tert-butyl-phenyl)-5-methyl-[1,2,4]triazolo[1,5-a]pyrimidine-7-ylamine with any one of the compounds of formula I compiled in table I.

Another preferred embodiment of the invention provides mixtures of 5-methyl-6-(3,5,5-trimethyl-hexyl)-[1,2,4]triazolo[1,5-a]pyrimidine-7-ylamine with any one of the compounds of formula I compiled in table I.

Another preferred embodiment of the invention provides mixtures of 5-methyl-6-octyl-[1,2,4]triazolo[1,5-a]pyrimidine-7-ylamine with any one of the compounds of formula I compiled in table I.

Another preferred embodiment of the invention provides mixtures of 6-methyl-5-octyl-[1,2,4]triazolo[1,5-a]pyrimidine-7-ylamine with any one of the compounds of formula I compiled in table I.

Another preferred embodiment of the invention provides mixtures of 6-ethyl-5-octyl-[1,2,4]triazolo[1,5-a]pyrimidine-7-ylamine with any one of the compounds of formula I compiled in table I.

Another preferred embodiment of the invention provides mixtures of 5-ethyl-6-octyl-[1,2,4]triazolo[1,5-a]pyrimidine-7-ylamine with any one of the compounds of formula I compiled in table I.

Another preferred embodiment of the invention provides mixtures of 5-ethyl-6-(3,5,5-trimethyl-hexyl)-[1,2,4]triazolo[1,5-a]pyrimidine-7-ylamine with any one of the compounds of formula I compiled in table I.

Another preferred embodiment of the invention provides mixtures of 6-octyl-5-propyl-[1,2,4]triazolo[1,5-a]pyrimidine-7-ylamine with any one of the compounds of formula I compiled in table I.

Another preferred embodiment of the invention provides mixtures of 5-methoxymethyl-6-octyl-[1,2,4]triazolo[1,5-a]pyrimidine-7-ylamine with any one of the compounds of formula I compiled in table I.

Another preferred embodiment of the invention provides mixtures of 6-octyl-5-trifluoromethyl-[1,2,4]triazolo[1,5-a]pyrimidine-7-ylamine with any one of the compounds of formula I compiled in table I.

Another preferred embodiment of the invention provides mixtures of 5-trifluoromethyl-6-(3,5,5-trimethyl-hexyl)-[1,2,4]triazolo[1,5-a]pyrimidine-7-ylamine with any one of the compounds of formula I compiled in table I.

For use according to the present invention, the mixtures according to the invention, or a compound I and an active compound II, can be converted into the customary formulations, for example solutions, emulsions, suspensions, dusts, powders, pastes and granules. The use form depends on the particular intended purpose; in each case, it should ensure a fine and even distribution of the compound according to the invention.

The formulations are prepared in a known manner, for example by extending the active compound with solvents and/or carriers, if desired using emulsifiers and dispersants. Solvents/auxiliaries which are suitable are essentially:

water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used, carriers such as ground natural minerals (for example kaolins, clays, talc, chalk) and ground synthetic minerals (for example highly disperse silica, silicates); emulsifiers such as nonionic and anionic emulsifiers (for example polyoxyethylene fatty alcohol ethers, alkylsulfonates and arylsulfonates) and dispersants such as lignosulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ethers, ethoxylated isooctylphenol, octylphenol, nonylphenol, alkylphenol polyglycol ethers, tributylphenyl polyglycol ethers, tristearylphenyl polyglycol ethers, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Also anti-freezing agents such as glycerin, ethylene glycol, propylene glycol and bactericides such as can be added to the formulation.

Suitable antifoaming agents are for example antifoaming agents based on silicon or magnesium stearate.

Suitable preservatives are for example Dichlorophen and enzylalkoholhemiformal. Seed Treatment formulations may additionally comprise binders and optionally colorants.

Binders can be added to improve the adhesion of the active materials on the seeds after treatment. Suitable binders are block copolymers EO/PO surfactants but also polyvinylalcoholsl, polyvinylpyrrolidones, polyacrylates, polymethacrylates, polybutenes, polyisoutylenes, polystyrene, polyethyleneamines, polyethyleneamides, polyethyleneimines (Lupasol®, Polymin®), polyethers, polyurethans, polyvinylacetate, tylose and copolymers derived from these polymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of a gelling agent is carrageen (Satiagel®)

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compound. The active compounds are employed in a purity of from 90% to 100%, preferably 95% to 100% (according to NMR spectrum).

For seed treatment purposes, respective formulations can be diluted 2-10 fold leading to concentrations in the ready to use preparations of 0.01 to 60% by weight active compound by weight, preferably 0.1 to 40% by weight.

The following are examples of formulations: 1. Products for dilution with water For seed treatment purposes, such products may be applied to the seed diluted or undiluted.

A Water-Soluble Concentrates (SL, LS)

10 parts by weight of the active compounds are dissolved with 90 parts by weight of water or a water-soluble solvent. As an alternative, wetters or other auxiliaries are added. The active compound dissolves upon dilution with water. A formulation having an active compound content of 10% by weight is obtained in this manner.

B Dispersible Concentrates (DC)

20 parts by weight of the active compounds are dissolved in 70 parts by weight of cyclohexanone with addition of 10 parts by weight of a dispersant, for example polyvinylpyrrolidone. Dilution with water gives a dispersion. The active compound content is 20% by weight.

C Emulsifiable Concentrates (EC)

15 parts by weight of the active compounds are dissolved in 75 parts by weight of xylene with addition of calcium dodecylbenzenesulfonate and castor oil ethoxylate (in each case 5 parts by weight). Dilution with water gives an emulsion. The formulation has an active compound content of 15% by weight.

D Emulsions (EW, EO, ES)

25 parts by weight of the active compounds are dissolved in 35 parts by weight of xylene with addition of calcium dodecylbenzenesulfonate and castor oil ethoxylate (in each case 5 parts by weight). This mixture is added into 30 parts by weight of water by means of an emulsifying machine (e.g. Ultraturrax) and made into a homogeneous emulsion. Dilution with water gives an emulsion. The formulation has an active compound content of 25% by weight.

E Suspensions (SC, OD, FS)

In an agitated ball mill, 20 parts by weight of the active compounds are comminuted with addition of 10 parts by weight of dispersants and wetters and 70 parts by weight of water or an organic solvent to give a fine active compound suspension. Dilution with water gives a stable suspension of the active compound. The active compound content in the formulation is 20% by weight.

F Water-Dispersible Granules and Water-Soluble Granules (WG, SG)

50 parts by weight of the active compounds are ground finely with addition of 50 parts by weight of dispersants and wetters and made into water-dispersible or water-soluble granules by means of technical appliances (for example extrusion, spray tower, fluidized bed). Dilution with water gives a stable dispersion or solution of the active compound. The formulation has an active compound content of 50% by weight.

G Water-Dispersible Powders and Water-Soluble Powders (WP, SP, SS, WS)

75 parts by weight of the active compounds are ground in a rotor-stator mill with addition of 25 parts by weight of dispersants and wetters as well as silica gel. Dilution with water gives a stable dispersion or solution of the active compound. The active compound content of the formulation is 75% by weight.

H Gel Formulations (GF)

In a ball mill, 20 parts by weight of the active compounds, 10 parts by weight of dispersant, 1 part by weight of gelling agent and 70 parts by weight of water or an organic solvent are ground to give a fine suspension. On dilution with water, a stable suspension having an active compound content of 20% by weight is obtained.

2. Products to be Applied Undiluted

I Dustable Powders (DP, DS)

5 parts by weight of the active compounds are ground finely and mixed intimately with 95 parts by weight of finely divided kaolin. This gives a dustable product having an active compound content of 5% by weight.

J Granules (GR, FG, GG, MG)

0.5 part by weight of the active compounds is ground finely and associated with 99.5 parts by weight of carriers. Current methods are extrusion, spray-drying or the fluidized bed. This gives granules to be applied undiluted having an active compound content of 0.5% by weight.

K ULV Solutions (UL)

10 parts by weight of the active compounds are dissolved in 90 parts by weight of an organic solvent, for example xylene. This gives a product to be applied undiluted having an active compound content of 10% by weight.

For seed treatment, use is usually made of water-soluble concentrates (LS), suspensions (FS), dustable powders (DS), water-dispersible and water-soluble powders (WS, SS), emulsions (ES), emulsifiable concentrates (EC) and gel formulations (GF). These formulations can be applied to the seed in undiluted form or, preferably, diluted. Application can be carried out prior to sowing.

In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

The active compounds can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; the intention is to ensure in each case the finest possible distribution of the active compounds according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier.

Alternatively, it is possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1%.

The active compounds may also be used successfully in the ultra-low-volume process (ULV), by which it is possible to apply formulations comprising over 95% by weight of active compound, or even to apply the active compound without additives.

Various types of oils, wetters, adjuvants, herbicides, fungicides, other pesticides, or bactericides may be added to the active compounds, if appropriate not until immediately prior to use (tank mix). These agents can be admixed with the agents according to the invention in a weight ratio of 1:100 to 100:1, preferably 1:10 to 10:1.

Compositions of this invention may also contain other active ingredients, for example other pesticides, herbicides, fertilizers such as ammonium nitrate, urea, potash, and superphosphate, phytotoxicants and plant growth regulators and safeners. These additional ingredients may be used sequentially or in combination with the above-described compositions, if appropriate also added only immediately prior to use (tank mix). For example, the plant(s) may be sprayed with a composition of this invention either before or after being treated with other active ingredients.

The compound I and the compound II can be applied in a weight ratio of from 5000:1 to 1:5000, preferably from 500:1 to 1:100, more preferably from 100:1 to 1:100, in particular from 20:1 to 1:20, most preferred from 10:1 to 1:10.

When preparing the mixtures, it is preferred to employ the pure active compounds I and II, to which further active compounds against harmful fungi or against other pests, such as insects, arachnids or nematodes, or else herbicidal or growth-regulating active compounds or fertilizers can be added as further active components according to need.

Usually, mixtures of a compound I with an active compound II are employed. However, in certain cases mixtures of the compound I with two or, if appropriate, more active components may be advantageous.

Suitable further active components in the above sense are in particular the active compounds II, mentioned at the outset and in particular the preferred active compounds mentioned above.

If more than one compound II is used according to the invention, the further active components are, if desired, added in a ratio of from 20:1 to 1:20 to the compound I.

Alternatively such further active compounds are applied in a weight ration from 20:1 to 1:20 to the compound II.

The mixtures of the compounds I and active compounds II are employed by treating the fungi or the plants, seeds, materials or soil to be protected from fungal attack with a fungicidally effective amount of the active compounds. The application can be carried out both before and after the infection of the materials, plants or seeds by the fungi.

In the method of combating harmful fungi depending on the type of compound and the desired effect, the application rates of the mixtures according to the invention are from 5 g/ha to 2000 g/ha, preferably from 50 to 900 g/ha, in particular from 50 to 750 g/ha.

Correspondingly, the application rates for the compound I are generally from 1 to 1000 g/ha, preferably from 10 to 900 g/ha, in particular from 20 to 750 g/ha.

Correspondingly, the application rates for the active compound II are generally from 1 to 2000 g/ha, preferably from 10 to 900 g/ha, in particular from 40 to 500 g/ha.

The method for controlling harmful fungi is carried out by the separate or joint application of a compound I and the active compound II or the mixtures of the compound I and the active compound II by spraying or dusting the seeds, the plants or the soil before or after sowing of the plants or before or after emergence of the plants.

The treatment can be made into the seedbox before planting into the field.

The mixtures of a compound I and at least a compound II or the simultaneous, that is joint or separate, use of a compound I and at least a compound II are distinguished by being highly active against a wide range of phytopathogenic fungi, in particular from the classes of the Ascomycetes, Deuteromycetes, Peronosporomycetes and Basidiomycetes. Some of them act systemically and can be used in crop protection as foliar fungicides, as fungicides for seed dressing and as soil-acting fungicides.

They are particularly important for controlling a multitude of fungi on various cultivated plants, such as bananas, cotton, vegetable species (for example cucumbers, beans and cucurbits), barley, grass, oats, coffee, potatoes, corn, fruit species, rice, rye, soya, tomatoes, grapevines, wheat, ornamental plants, sugar cane and also on a large number of seeds.

The compounds I and the compounds II can be applied simultaneously, that is jointly or separately, or in succession, the sequence, in the case of separate application, generally not having any effect on the result of the control measures.

They are particularly important in the control of a multitude of fungi on various cultivated plants, such as wheat, rye, barley, oats, rice, corn, grass, bananas, cotton, soybeans, coffee, sugar cane, vines, fruits and ornamental plants, and vegetables, such as cucumbers, beans, tomatoes, potatoes and cucurbits, and on the seeds of these plants. They can also be used in crops which are tolerant to insect or fungal attack because of breeding, including genetic engineering methods. Moreover, they are suitable for controlling *Botryosphaeria* species, *Cylindrocarpon* species, *Eutypa lata*, *Neonectria liriodendri* and *Stereum hirsutum* which infest inter alia the wood or the roots of grapevines.

They are especially suitable for controlling each of the following plant diseases:

*Alternaria* species on vegetables, rapeseed, sugar beet, fruit, rice, soybeans and on potatoes (for example *A. solani* or *A. alternata*) and tomatoes (for example *A. solani* or *A. alternata*) and *Alternaria* ssp. (black head mold) on wheat,

*Aphanomyces* species on sugar beet and vegetables,

*Ascochyta* species on cereals and vegetables, for example *Ascochyta tritici* (leaf spot) on wheat,

*Bipolaris* and *Drechslera* species on corn (for example, *D. maydis*), cereals, rice and lawn,

*Blumeria graminis* (powdery mildew) on cereals (for example wheat or barley),

*Botrytis cinerea* (gray mold) on strawberries, vegetables, flowers, grapevines and wheat (head mold),

*Bremia lactucae* on lettuce,

*Cercospora* species on corn, rice, sugar beet, and e.g. *Cercospora sojina* (leaf spot) or *Cercospora kikuchii* (leaf spot) on soybeans,

*Cladosporium herbarum* (ear rot) on wheat,

*Cochliobolus* species on corn, cereals (e.g. *Cochliobolus sativus*) and rice (e.g. *Cochliobolus miyabeanus*),

*Colletotricum* species on cotton and e.g. *Colletotrichum truncatum* (anthracnose) on soybeans,

*Corynespora cassiicola* (leaf spot) on soybeans,

*Dematophora necatrix* (root/stem rot) on soybeans,

*Diaporthe phaseolorum* (stem disease) on soybeans,

*Drechslera* species, *Pyrenophora* species on corn, cereals, rice and lawn, on barley (for example, *D. teres*) or on wheat (for example *D. tritici-repentis*), Esca on grapevines, caused by *Phaeoacremonium chlamydosporium*, *Ph. Aleophilum*, and *Formitipora punctata* (syn. *Phellinus punctatus*),

*Elsinoe empelina* on grapevines,

*Epicoccum* spp. (black head mold) on wheat,

*Exserohilum* species on corn,

*Erysiphe cichoracearum* and *Sphaerotheca fuliginea* on cucumbers,

*Fusarium* and *Verticillium* species on various plants: for example, *F. graminearum* or *F. culmorum* (root rot) on cereals (for example wheat or barley) or for example *F. oxysporum* on tomatoes,
and *Fusarium solani* (stem disease) on soybeans,
*Gaeumanomyces graminis* (root black) on cereals (for example wheat or barley),
*Gibberella* species on cereals and rice (for example *Gibberella fujikuroi*),
*Glomerella cingulata* on grapevines and other plants,
Grainstaining complex on rice,
*Guignardia budwelli* on grapevines,
*Helminthosporium* species on corn and rice,
*Isariopsis clavispora* on grapevines,
*Macrophomina phaseolina* (root/stem rot) on soybeans,
*Michrodochium nivale* (snow mold) on cereals (for example wheat or barley),
*Microsphaera difusa* (powdery mildew) on soybeans,
*Mycosphaerella* species on cereals, bananas and peanuts, such as, for example, *M. graminicola* on wheat or *M. fijiensis* on bananas,
*Peronospora* species on cabbage (for example *P. brassicae*), onions, (for example, *P. destructor*) and for example *Peronospora manshurica* (downy mildew) on soybeans,
*Phakopsara pachyrhizi* (soybean rust) and *Phakopsara meibomiae* (soybean rust) on soybeans,
*Phialophora gregata* (stem disease) on soybeans,
*Phomopsis* species on sunflowers, grapevines (for example *P. viticola*) and soybeans (for example *Phomopsis phaseo*),
*Phytophthora* species on various plants, for example *P. capsicion* bell pepper, *Phytopthora megasperma* (leaf/stem rot) on soybeans, *Phytophthora infestans* on potatoes and tomatoes,
*Plasmopara viticola* on grapevines,
*Podosphaera leucotricha* on apples,
*Pseudocercosporella herpotrichoides* (eyespot) on cereals (wheat or barley),
*Pseudoperonospora* on various plants, for example *P. cubensis* on cucumber or *P. humili* on hops,
*Pseudopezicula tracheiphilai* on grapevines,
*Puccinia* species on various plants, for example *P. triticina, P. striformins, P. hordei* or *P. graminis* on cereals (for example wheat or barley) or on asparagus (for example *P. asparagi*),
*Pyricularia oryzae, Corticium sasakii, Sarocladium oryzae, S. attenuatum, Pyrenophora tritici-repentis* (leaf spot) on wheat or *Pyrenophora teres* (net spot) on barley, *Entyloma oryzae* on rice,
*Pyricularia grisea* on lawn and cereals,
*Pythium* spp. on lawn, rice, corn, wheat, cotton, oilseed rape, sunflowers, sugar beet, vegetables and other plants (for example *P. ultiumum* or *P. aphanidermatum*),
*Ramularia collo-cygni* (*Ramularia*/sunburn complex/physiological leaf spots) on barley,
*Rhizoctonia* species on cotton, rice, potatoes, lawn, corn, oilseed rape, potatoes, sugar beet, vegetables and on various other plants, for example *Rhizoctonia solani* (root/stem rot) on soybeans or *Rhizoctonia cerealis* (sharp eyespot) on wheat or barley,
*Rhynchosporium secalis* on barley (leaf spot), rye and triticale,
*Sclerotinia* species on oilseed rape, sunflowers and, for example *Sclerotinia scerotiorum* (stem disease) or *Sclerotinia rolfsii* (stem disease) on soybeans,
*Septoria glycines* (leaf spot) on soybeans,
*Septoria tritici* (leaf *septoria*) and *Stagonospora nodorum* on wheat,
*Erysiphe* (syn. *Uncinula*) *necator* on grapevines,
*Setospaeria* species on corn and lawn,
*Sphacelotheca reilinia* on corn,
*Stagonospora nodorum* (ear *septoria*) on wheat,
*Thievaliopsis* species on soybeans and cotton,
*Tilletia* species on cereals,
*Typhula incarnata* (snow rot) on wheat or barley,
*Ustilago* species on cereals, corn (for example *U. maydis*) and sugar cane,
*Venturia* species (scab) on apples (for example *V. inaequalis*) and pears.

The target crops may be crops of conventional plants or crops of genetically modified plants ("GM plants" or "GMOs").

The compositions according to the invention are therefore also suitable for use in herbicide-resistant, pest-resistant and/or fungus-resistant transgenic crops of useful plants, especially cereals, cotton, soybeans, sugar beet, sugar cane, plantation crops (e.g. citrus fruits, coffee, bananas), rape, maize and rice.

Herbicide-resistant crops are to be understood as including those that have been made tolerant to herbicides or classes of herbicides (e.g. ALS-, GS-, EPSPS-, PPO- and HPPD-inhibitors) by means of conventional breeding or genetic engineering methods. An example of a crop that has been made tolerant by conventional breeding methods to, for example, imidazolinones such as imazamox is Clearfield® summer rape (canola). Examples of crops made tolerant to herbicides by genetic engineering methods are maize varieties resistant to, for example, glyphosate or glufosinate, which are commercially available under the trade names RoundupReady® and LibertyLink®, respectively.

In the context of the present invention, pest-resistant and/or fungus-resistant transgenic useful plants are expressly understood to include those useful plants which, in addition to having the pest resistance and/or fungus resistance, also have herbicide tolerance. Among the group of herbicide-tolerant useful plants preference is given, in accordance with the invention, to useful plants having tolerance with respect to glyphosate, glufosinate-ammonium, ALS (acetolactate synthase) inhibitors, such as sulfonylureas, e.g. primisulfuron, prosulfuron and trifloxysulfuron, or bromoxynil, such as, for example, Bt11 maize or Herculex I® maize.

Pest-resistant transgenic crop plants are to be understood in the context of the present invention as being plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, e.g. insecticidal proteins from *Bacillus cereus* or *Bacillus popliae*; or insecticidal proteins from *Bacillus thuringiensis*, such as alpha-endotoxins, e.g. CryIA(b), CryIA(c), CryIF, CryIF(a2), CryIA(b), CryIIIA, CryIIIB(bi) or Cry9c, or vegetative insecticidal proteins (VIP), e.g. VIP1, VIP2, VIP3 or VIP3A; or insecticidal proteins of bacteria that colonise nematodes, for example *Photorhabdus* spp. or *Xenorhabdus* spp., such as *Photorhabdus luminescens, Xenorhabdus nematophilus*, toxins produced by animals, such as scorpion toxins, arachnid toxins, wasp toxins and other insect-specific neurotoxins; toxins produced by fungi, such as *Streptomycetes* toxins; plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroid-oxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by d-endotoxins, for example CryIA(b), CryIA(c), CryIF, CryIF(a2), CryIIA(b), CryIIIA, CryIIIB(bi) or Cry9c, or vegetative insecticidal proteins (VIP), for example VIP1, VIP2, VIP3 or VIP3A, expressly also hybrid toxins, truncated toxins and modified toxins. Hybrid toxins are produced recombinantly by a new combination of different domains of those proteins (see, for example, WO 02/15701). An example of a truncated toxin is a truncated CryIA(b), which is expressed in Bt11 maize of Syngenta Seeds SAS, as described hereinbelow. In the case of modified toxins, one or more amino acids of the naturally occurring toxin is/are replaced. In such amino acid replacements, preferably nonnaturally present protease recognition sequences are inserted into the toxin, such as, for example, in the case of CryIIIA055, a cathepsin-D-recognition sequence is inserted into a CryIIIA toxin (see WO 03/018810).

Examples of such toxins or transgenic plants capable of synthesising such toxins are disclosed, for example, in EP-A 374 753, WO 93/07278, WO 95/34656, EP-A 427 529, EP-A 451 878 and WO 03/052073.

The processes for the production of such transgenic plants are generally known to the person skilled in the art and are described, for example, in the publications mentioned above. CryI-type deoxyribonucleic acids and their preparation are known, for example, from WO 95/34656, EP-A 367 474, EP-A 401 979 and WO 90/13651.

The toxin contained in the transgenic plants provides the plants with tolerance to harmful insects. Such insects can occur in any taxonomic group of insects, but are especially commonly found in beetles (Coleoptera), two-winged insects (Diptera) and butterflies (Lepidoptera).

The following harmful insects from different taxonomic groups are especially common in maize crops:
*Ostrinia nubilalis*, European corn borer,
*Agrotis ipsilon*, black cutworm,
*Helicoverpa zea*, corn earworm,
*Spodoptera frugiperda*, fall armyworm,
*Diatraea grandiosella*, southwestern corn borer,
*Elasmopalpus lignosellus*, lesser cornstalk borer,
*Diatraea saccharalis*, sugarcane borer,
*Diabrotica virgifera virgifera*, western corn rootworm,
*Diabrotica longicornis barberi*, northern corn rootworm,
*Diabrotica undecimpunctata howardi*, southern corn rootworm,
*Melanotus* spp., wireworms,
*Cyclocephala borealis*, northern masked chafer (white grub),
*Cyclocephala immaculata*, southern masked chafer (white grub),
*Popillia japonica*, Japanese beetle,
*Chaetocnema pulicaria*, corn flea beetle,
*Sphenophorus maidis*, maize billbug,
*Rhopalosiphum maidis*, corn leaf aphid,
*Anuraphis maidiradicis*, corn root aphid,
*Blissus leucopterus leucopterus*, chinch bug,
*Melanoplus femurrubrum*, red-legged grasshopper,
*Melanoplus sanguinipes*, migratory grasshopper,
*Hylemya platura*, seedcorn maggot,
*Agromyza parvicornis*, corn blotch leafminer,
*Anaphothrips obscurus*, grass thrips,
*Solenopsis milesta*, thief ant,
*Tetranychus urticae*, two-spotted spider mite.

Transgenic plants containing one or more genes that code for an insecticidal resistance and express one or more toxins are known and some of them are commercially available. Examples of such plants are: YieldGard® (maize variety that expresses a CryIA(b) toxin); YieldGard Rootworm® (maize variety that expresses a CryIIIB(bi) toxin); YieldGard Plus® (maize variety that expresses a CryIA(b) and a CryIIIB(bi) toxin); Starlink® (maize variety that expresses a Cry9(c) toxin); Herculex I® (maize variety that expresses a CryIF(a2) toxin and the enzyme phosphinothricin N-acetyl-transferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); NatureGard® and Protecta®.

Further examples of such transgenic crops are:
1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated CryIA(b) toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR96/05/10. Genetically modified *Zea mays* which has been rendered resistant to attack by the European corn borer (*Ostrinia nuhilalis* and *Sesamia nonagrioides*) by transgenic expression of a CryIA(b) toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified CryIHA toxin. This toxin is Cry3A055 modified by insertion of a cathepsin-D-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a CryIIIB(bi) toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NLJ00/10. Genetically modified maize for the expression of the protein Cry1 F for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup (contains glyphosate), and also a CryIA(b) toxin obtained from *Bacillus thuringiensis* subsp. *kurstaki* which brings about tolerance to certain Lepidoptera, including the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

In the context of the present invention, fungus-resistant transgenic crop plants are to be understood as being those which have been so transformed by the use of recombinant DNA techniques that they are capable of synthesising antipathogenic substances having a selective action, such as, for example, the so-called "pathogenesis-related proteins" (PRPs, see e.g. EP-A 392 225). Examples of such antipathogenic substances and transgenic plants capable of synthesising such antipathogenic substances are known, for example, from EP-A 392 225, WO 95/33818 and EP-A 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906). Further areas of use of the compositions according to the invention are the protection of stored goods and storerooms and the protection of raw materials, such as wood, textiles, floor coverings or buildings, and also in the hygiene sector, especially the protection of humans, domestic animals and productive livestock against pests of the mentioned type.

In the context of the invention transgenic plants may contain one or more genes that code for an insecticidal resistance as well as for a herbicidal resistance, as described above (e.g. RR Bollguard® or RR Yieldguard® traits). Those are considered transgenic plants containing a double or even triple stacked genes. Furthermore, this concept of multiple stacking of genes or events in a transgenic plant can be considered also for a broader and larger application, such as fungicidal resistance or drought resistance. The latter are to be understood of which have been so transformed by the use of recombinant DNA techniques that they are capable providing stress resistance under drought selection pressure to the crop plant. Furthermore, genes which increase the yield potential of a given crop plant per se, when introduced by transformation technologies with the use of recombinant DNA, providing additional yield by modifying a given physiological pathway of the crop plant, have to be considered in the multiple stacking concept of transgenic crop plants, e.g. RR2Yield® in soybean.

The compounds I and II or the mixtures or the corresponding formulations are applied by treating the harmful fungi, the plants, seeds, soils, areas, materials or spaces to be kept free from them with a fungicidally effective amount of the mixture or, in the case of separate application, of the compounds I and II. Application can be carried out before or after infection by the harmful fungi.

The mixtures of compounds I and II, or the compounds I and II used simultaneously, that is jointly or separately, exhibit also outstanding action against pests from the following orders:

insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis*, beetles (Coleoptera), for example *Agrilus sinuatus, Agriotes lineatus, Agriotes obscurus, Amphimallus solstitialis, Anisandrus dispar, Anthonomus grandis, Anthonomus pomorum, Aphthona euphoridae, Athous haemorrhoidalis, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema tibialis, Conoderus vespertinus, Crioceris asparagi, Ctenicera* ssp., *Diabrotica longicornis, Diabrotica semipunctata, Diabrotica 12-punctata Diabrotica speciosa, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastan, Melolontha melolontha, Oulema oryzae, Ortiorrhynchus sulcatus, Otiorrhynchus ovatus, Phaedon cochleariae, Phyllobius pyri, Phyllotreta chrysocephala, Phyllophaga* sp., *Phyllopertha horticola, Phyllotreta nemorum, Phyllotreta striolata, Popillia japonica, Sitona lineatus* and *Sitophilus granaria*, flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifoli, Lucilia caprina, Lucilia cuprina, Lucilia sericata, Lycoria pectoralis, Manso-*

*nia titillanus, Mayetiola destructor, Musca domestica, Muscina stabulans, Oestrus ovis, Opomyza florum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga* sp., *Simulium vittatum, Stomoxys calcitrans, Tabanus bovinus, Tabanus atratus, Tabanus lineola,* and *Tabanus similis, Tipula oleracea,* and *Tipula paludosa* thrips (Thysanoptera), e.g. *Dichromothrips corbetti, Dichromothrips* ssp, *Frankliniella fusca, Frankliniella occidentalis, Frankliniella tritici, Scirtothrips citrci, Thrips oryzae, Thrips palmi* and *Thrips tabac* termites (Isoptera), e.g. *Calotermes flavicollis, Leucotermes flavipes, Heterotermes aureus, Reticulitermes flavipes, Reticulitermes virginicus, Reticulitermes lucifugus, Termes natalensis,* and *Coptotermes formosanus,* cockroaches (Blattaria—Blattodea), e.g. *Battella germanica, Battella asahinae, Periplaneta americana, Periplaneta japonica, Periplaneta brunnea, Periplaneta fuligginosa, Periplaneta australasiae,* and *Blatta orientalis,* true bugs (Hemiptera), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor, Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus horni, Cerosipha gossypi, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzus persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand, Viteus vitifolii, Cimex lectularius, Cimex hemipterus, Reduvius senilis, Triatoma* spp., and *Arilus critatus.* ants, bees, wasps, sawflies (Hymenoptera), e.g. *Athalia rosae, Atta cephalotes, Atta capiguara, Atta cephalotes, Atta laevigata, Atta robusta, Atta sexdens, Atta texana, Crematogaster* spp., *Hoplocampa minuta, Hoplocampa testudinea, Monomorium pharaonis, Solenopsis geminata, Solenopsis invicta, Solenopsis richteri, Solenopsis xyloni, Pogonomyrmex barbatus, Pogonomyrmex californicus, Pheidole megacephala, Dasymutilla occidentalis, Bombus* spp. *Vespula squamosa, Paravespula vulgaris, Paravespula pennsylvanica, Paravespula germanica, Dolichovespula maculata, Vespa crabro, Polistes rubiginosa, Camponotus floridanus,* and *Linepithema humile,* crickets, grasshoppers, locusts (Orthoptera), e.g. *Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria angulifera, Calliptamus italicus, Chortoicetes terminifera,* and *Locustana pardalina,*

Arachnoidea, such as arachnids (Acarina), e.g. of the families Argasidae, Ixodidae and Sarcoptidae, such as *Amblyomma americanum, Amblyomma variegatum, Ambryomma maculatum, Argas persicus, Boophilus annulatus, Boophilus decoloratus, Boophilus microplus, Dermacentor silvarum, Dermacentor andersoni, Dermacentor variabilis, Hyalomma truncatum, Ixodes ricinus, Ixodes rubicundus, Ixodes scapularis, Ixodes holocyclus, Ixodes pacificus, Ornithodorus moubata, Ornithodorus hermsi, Ornithodorus turicata, Ornithonyssus bacoti, Otobius megnini, Dermanyssus gallinae, Psoroptes ovis, Rhipicephalus sanguineus, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni; Tarsonemidae* spp. such as *Phytonemus pallidus* and *Polyphagotarsonemus latus, Tenuipalpidae* spp. such as *Brevipalpus phoenicis; Tetranychidae* spp. such as *Tetranychus cinnabarinus, Tetranychus kanzawai, Tetranychus pacificus, Tetranychus telarius* and *Tetranychus urticae, Panonychus ulmi, Panonychus citri,* and *Oligonychus pratensis*; Araneida, e.g. *Latrodectus mactans,* and *Loxosceles reclusa,* fleas (Siphonaptera), e.g. *Ctenocephalides felis, Ctenocephalides canis, Xenopsylla cheopis, Pulex irritans, Tunga penetrans,* and *Nosopsyllus fasciatus,* silverfish, firebrat (Thysanura), e.g. *Lepisma saccharina* and *Thermobia domestica,* centipedes (Chilopoda), e.g. *Scutigera coleoptrata,* millipedes (Diplopoda), e.g. *Narceus* spp.,

Earwigs (Dermaptera), e.g. *forficula auricularia,* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus,* plant parasitic nematodes such as root-knot nematodes, *Meloidogyne arenaria, Meloidogyne chitwoodi, Meloidogyne exigua, Meloidogyne hapla, Meloidogyne incognita, Meloidogyne javanica* and other *Meloidogyne* species; cyst nematodes, *Globodera rostochiensis, Globodera pallida, Globodera tabacum* and other *Globodera* species, *Heterodera avenae, Heterodera glycines, Heterodera schachtii, Heterodera trifolii,* and other *Heterodera* species, seed gall nematodes, *Anguina funesta, Anguina tritici* and other *Anguina* species; stem and foliar nematodes, *Aphelenchoides besseyi, Aphelenchoides fragariae, Aphelenchoides ritzemabosi* and other *Aphelenchoides* species; sting nematodes, *Belonolaimus longicaudatus* and other *Belonolaimus* species; pine nematodes, *Bursaphelenchus xylophilus* and other *Bursaphelenchus* species, ring nematodes, *Criconema* species, *Criconemella* species, *Criconemoides* species, and *Mesocriconema* species; stem and bulb nematodes, *Ditylenchus destructor, Ditylenchus dipsaci, Ditylenchus myceliophagus* and other *Ditylenchus* species; awl nematodes, *Dolichodorus* species; spiral nematodes, *Helicotylenchus dihystera, Helicotylenchus multicinctus* and other *Helicotylenchus* species, *Rotylenchus robustus* and other *Rotylenchus* species; sheath nematodes, *Hemicycliophora* species and *Hemicriconemoides* species; *Hirshmanniella* species, lance nematodes, *Hoplolaimus columbus, Hoplolaimus galeatus* and other *Hoplolaimus* species, false root-knot nematodes, *Nacobbus aberrans* and other *Nacobbus* species; needle nematodes, *Longidorus elongates* and other *Longidorus* species; pin nematodes, *Paratylenchus* species; lesion nematodes, *Pratylenchus brachyurus, Pratylenchus coffeae, Pratylenchus curvitatus, Pratylenchus goodeyi, Pratylencus neglectus, Pratylenchus penetrans, Pratylenchus scribneri, Pratylenchus vulnus, Pratylenchus zeae* and other *Pratylenchus* species, *Radinaphelenchus cocophilus* and other *Radinaphelenchus* species; burrowing nematodes, *Radopholus similis* and other *Radopholus* species; reniform nematodes, *Rotylenchulus reniformis* and other *Rotylenchulus* species, *Scutellonema* species, stubby root nematodes, *Trichodorus primitivus* and other *Trichodorus* species; *Paratrichodorus minor* and other *Paratrichodorus* species; stunt nematodes, *Tylenchorhynchus claytoni, Tylenchorhynchus dubius* and other *Tylenchorhynchus* species and *Merlinius* species, citrus nematodes, *Tylenchulus semipenetrans* and other *Tylenchulus* species, dagger nematodes, *Xiphinema americanum, Xiphinema index, Xiphinema diversicaudatum* and other *Xiphinema* species; and other plant parasitic nematode species.

Moreover, the inventive mixtures are especially useful for the control of Lepidoptera, Coleoptera, Diptera, Thysanoptera and Hymenoptera.

Moreover, the inventive mixtures are especially useful for the control of non-crop pests (household, turf, ornamental).

The mixtures according to the invention can be applied to any and all developmental stages of pests, such as egg, larva, pupa, and adult. The pests may be controlled by contacting the target pest, its food supply, habitat, breeding ground or its locus with a pesticidally effective amount of the inventive mixtures or of compositions comprising the mixtures.

"Locus" means a plant, seed, soil, area, material or environment in which a pest is growing or may grow.

In general, "pesticidally effective amount" means the amount of the inventive mixtures or of compositions comprising the mixtures needed to achieve an observable effect on growth, including the effects of necrosis, death, retardation, prevention, and removal, destruction, or otherwise diminishing the occurrence and activity of the target organism. The pesticidally effective amount can vary for the various mixtures/compositions used in the invention. A pesticidally effective amount of the mixtures/compositions will also vary according to the prevailing conditions such as desired pesticidal effect and duration, weather, target species, locus, mode of application, and the like.

The inventive mixtures or compositions of these mixtures can also be employed for protecting plants from attack or infestation by insects, acarids or nematodes comprising contacting a plant, or soil or water in which the plant is growing.

In the context of the present invention, the term plant refers to an entire plant, a part of the plant or the propagation material of the plant, that is, the seed or the seedling.

Plants which can be treated with the inventive mixtures include all genetically modified plants or transgenic plants, e.g. crops which tolerate the action of herbicides or fungicides or insecticides owing to breeding, including genetic engineering methods, or plants which have modified characteristics in comparison with existing plants, which can be generated for example by traditional breeding methods and/or the generation of mutants, or by recombinant procedures.

Some of the inventive mixtures have systemic action and can therefore be used for the protection of the plant shoot against foliar pests as well as for the treatment of the seed and roots against soil pests. The term seed treatment comprises all suitable seed treatment techniques known in the art, such as seed dressing, seed coating, seed dusting, seed soaking and seed pelleting.

The compounds I and the one or more compound(s) II can be applied simultaneously, that is jointly or separately, or in succession, the sequence, in the case of separate application, generally not having any effect on the result of the control measures.

The compounds I and the one or more compound(s) II can generally be applied in a weight ratio of rom 5000:1 to 1:5000, usually in from 500:1 to 1:100, preferably from 20:1 to 1:50, in particular from 5:1 to 1:20.

Depending on the desired effect, the application rates of the mixtures according to the invention are from 5 g/ha to 2000 g/ha, preferably from 50 to 1500 g/ha, in particular from 50 to 750 g/ha.

The inventive mixtures are also suitable for the protection of the seed and the seedlings' roots and shoots, preferably the seeds, against soil pests.

Compositions, which are especially useful for seed treatment are e.g.:

A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter. Preferred are FS formulations.

In the treatment of seed, the application rates of the inventive mixture are generally from 0.001 to 10 kg per 100 kg of seed, dependent from the desired effect and the kind of seed. Application rates are preferably from 1 to 1000 g/100 kg of seed, more preferably from 1 to 750 g/100 kg, in particular from 5 to 500 g/100 kg. The separate or joint application of the compounds I and II or of the mixtures of the compounds I and II is carried out by spraying or dusting the seeds, the seedlings, the plants or the soils before or after sowing of the plants or before or after emergence of the plants.

The invention also relates to the propagation products of plants, and especially the seed comprising, that is, coated with and/or containing, a mixture as defined above or a composition containing the mixture of two or more active ingredients or a mixture of two or more compositions each providing one of the active ingredients. The seed comprises the inventive mixtures in an amount of from 0.1 g to 10 kg per 100 kg of seed.

The inventive mixtures are effective through both contact (via soil, glass, wall, bed net, carpet, plant parts or animal parts), and ingestion (bait, or plant part) and through trophallaxis and transfer.

Preferred application methods are into water bodies, via soil, cracks and crevices, pastures, manure piles, sewers, into water, on floor, wall, or by perimeter spray application and bait.

According to another preferred embodiment of the invention, for use against non crop pests such as ants, termites, wasps, flies, mosquitoes, crickets, locusts, or cockroaches the inventive mixtures are prepared into a bait preparation.

The bait can be a liquid, a solid or a semisolid preparation (e.g. a gel). The bait employed in the composition is a product which is sufficiently attractive to incite insects such as ants, termites, wasps, flies, mosquitoes, crickets etc. or cockroaches to eat it. This attractant may be chosen from feeding stimulants or para and/or sex pheromones readily known in the art.

Methods to control infectious diseases transmitted by insects (e.g. malaria, dengue and yellow fever, lymphatic filariasis, and leishmaniasis) with the inventive mixtures and their respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a composition including the inventive mixtures, optionally a repellent and at least one binder.

The inventive mixtures and the compositions comprising them can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities).

In the case of soil treatment or of application to the pests dwelling place or nest, the quantity of active ingredient ranges from 0.0001 to 500 g per 100 $m^2$, preferably from 0.001 to 20 g per 100 $m^2$.

Customary application rates in the protection of materials are, for example, from 0.01 g to 1000 g of active compound per $m^2$ treated material, desirably from 0.1 g to 50 g per $m^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in bait compositions, the typical content of active ingredient is from 0.0001 weight % to 15 weight %, desirably from 0.001 weight % to 5% weight % of active compound. The composition used may also comprise other additives such as a solvent of the active material, a flavoring agent, a preserving agent, a dye or a bitter agent. Its attractiveness may also be enhanced by a special color, shape or texture.

For use in spray compositions, the content of the mixture of the active ingredients is from 0.001 to 80 weights %, preferably from 0.01 to 50 weight % and most preferably from 0.01 to 15 weight %.

For use in treating crop plants, the rate of application of the mixture of the active ingredients of this invention may be in the range of 0.1 g to 4000 g per hectare, desirably from 25 g to 600 g per hectare, more desirably from 50 g to 500 g per hectare.

It was also an object of the present invention to provide mixtures suitable for treating, controlling, preventing and protecting warm-blooded animals, including humans, and fish against infestation and infection by pests. Problems that may be encountered with pest control on or in animals and/or humans are similar to those described at the outset, namely the need for reduced dosage rates, and/or enhanced spectrum of activity and/or combination of knock-down activity with prolonged control and/or resistance management.

This invention also provides a method for treating, controlling, preventing and protecting warm-blooded animals, including humans, and fish against infestation and infection by pests of the orders Siphonaptera, Hymenoptera, Hemiptera, Orthoptera, Acarina, Phthiraptera, and Diptera, which comprises orally, topically or parenterally administering or applying to said animals a pesticidally effective amount of mixtures according to the invention.

The invention also provides a process for the preparation of a composition for treating, controlling, preventing or protecting a warm-blooded animal or a fish against infestation or infection by pests of the Siphonaptera, Hymenoptera, Hemiptera, Orthoptera, Acarina, Phthiraptera, and Diptera orders which comprises a pesticidally effective amount of a mixture according to the invention.

The above method is particularly useful for controlling and preventing infestations and infections in warm-blooded animals such as cattle, sheep, swine, camels, deer, horses, poultry, goats, dogs and cats as well as humans.

Infestations in warm-blooded animals and fish including, but not limited to, lice, biting lice, ticks, nasal bots, keds, biting flies, muscoid flies, flies, myiasitic fly larvae, chiggers, gnats, mosquitoes and fleas may be controlled, prevented or eliminated by the mixtures according to the invention.

For oral administration to warm-blooded animals, the mixtures according to the invention may be formulated as animal feeds, animal feed premixes, animal feed concentrates, pills, solutions, pastes, suspensions, drenches, gels, tablets, boluses and capsules. In addition, the mixtures according to the invention may be administered to the animals in their drinking water. For oral administration, the dosage form chosen should provide the animal with 0.01 mg/kg to 100 mg/kg of animal body weight per day of the mixture.

Alternatively, the mixtures according to the invention may be administered to animals parenterally, for example, by intraruminal, intramuscular, intravenous or subcutaneous injection. The mixtures according to the invention may be dispersed or dissolved in a physiologically acceptable carrier for subcutaneous injection. Alternatively, the mixtures according to the invention may be formulated into an implant for subcutaneous administration. In addition the mixtures according to the invention may be transdermally administered to animals. For parenteral administration, the dosage form chosen should provide the animal with 0.01 mg/kg to 100 mg/kg of animal body weight per day of the mixture.

The mixtures according to the invention may also be applied topically to the animals in the form of dips, dusts, powders, collars, medallions, sprays, spot-on and pour-on formulations. For topical application, dips and sprays usually contain 0.5 ppm to 5,000 ppm and preferably 1 ppm to 3000 ppm of the inventive compounds. In addition, the mixtures according to the invention may be formulated as ear tags for animals, particularly quadrupeds such as cattle and sheep.

BIOLOGICAL EXAMPLES

1) Fungicidal Action

The fungicidal effect of the compound and the mixtures could be demonstrated by the following tests:
The active compounds, separately or jointly, were prepared as a stock solution comprising 0.25% by weight of active compound in acetone or DMSO. 1% by weight of the emulsifier Uniperol® EL (wetting agent having emulsifying and dispersant action based on ethoxylated alkylphenols) was added to this solution, and the mixture was diluted with water to the desired concentration.

The visually determined percentages of infected leaf areas were converted into efficacies in % of the untreated control: The efficacy (E) is calculated as follows using Abbot's formula:

$$E=(1-\alpha/\beta)\cdot 100$$

α corresponds to the fungicidal infection of the treated plants in % and

β corresponds to the fungicidal infection of the untreated (control) plants in %

An efficacy of 0 means that the infection level of the treated plants corresponds to that of the untreated control plants; an efficacy of 100 means that the treated plants were not infected.

The expected efficacies of mixtures of active compounds were determined using Colby's formula (Colby, S. R. "Calculating synergistic and antagonistic responses of herbicide Combinations", Weeds, 15, 20-22, 1967) and compared with the observed efficacies.

Colby's formula:

$$E = x + y - x \cdot y / 100$$

E expected efficacy, expressed in % of the untreated control, when using the mixture of the active compounds A and B at the concentrations a and b x efficacy, expressed in % of the untreated control, when using the active compound A at the concentration a y efficacy, expressed in % of the untreated control, when using the active compound B at the concentration b Use Example 1

Fungicidal Control of Brown Spot Caused by *Cochliobolus miyabeanus* (Protective)

Leaves of pot-grown rice seedlings were sprayed to run-off with an aqueous suspension, containing the concentration of active ingredient as described below prepared from the stock solution. The plants were allowed to air-dry. At the following day the plants were inoculated with an aqueous spore suspension of *Cochliobolus miyabeanus*. Then the trial plants were immediately transferred to a humid chamber. After 6 days at 22-24° C. and a relative humidity close to 100% the extent of fungal attack on the leaves was visually assessed as % diseased leaf area.

The test results show that, by virtue of strong synergism, the activity of the mixtures according to the invention is considerably higher than had been predicted using Colby's formula.

2) Action Against Animal Pests

The following tests demonstrate the control efficacy of compounds, mixtures or compositions of this invention on specific pests. However, the pest control protection afforded by the compounds, mixtures or compositions is not limited to these species. In certain instances, combinations of a compound of this invention with other invertebrate pest control compounds or agents are found to exhibit synergistic effects against certain important invertebrate pests.

The analysis of synergism or antagonism between the mixtures or compositions was determined using Colbys equation.

Use Example 2

For evaluating control of vetch aphid (*Megoura viciae*) through contact or systemic means the test unit consisted of 24-well-microtiter plates containing broad bean leaf disks.

The compounds or mixtures were formulated using a solution containing 75% water and 25% DMSO. Different concentrations of formulated compounds or mixtures were sprayed onto the leaf disks at 2.5 µl, using a custom built micro atomizer, at two replications.

For experimental mixtures in these tests identical volumes of both mixing partners at the desired concentrations respectively, were mixed together.

After application, the leaf disks were air-dried and 5-8 adult aphids placed on the leaf disks inside the microtiter plate wells. The aphids were then allowed to suck on the treated leaf disks and incubated at 23+1° C., 50+5% RH for 5 days. Aphid mortality and fecundity was then visually assessed.

In this test the compound I-2, and N-(3',4'-dichloro-5-fluorobiphenyl-2-yl)-3-difluoromethyl-1-methylpyrazole-4-carboxamide (compound 2.1), and 5-chloro-7-(4-methylpiperidin-1-yl)-6-(2,4,6-trifluorophenyl)-[1,2,4]triazolo[1,5-a]pyrimidine (compound 2.2) were used.

Following results were obtained

| Vetch Aphid | ppm | Average Control % |
| --- | --- | --- |
| I-2 | 0.5 | 0 |
| I-2 | 2.5 | 0 |
| 2.1 | 1000 | 0 |
| 2.2 | 40 | 0 |
| I-2 + 2.1 | 0.5 + 1000 | 100* |
| I-2 + 2.2 | 2.5 + 40 | 75* |

*synergistic control effect according to Colby's equation

Use Example 3

For evaluating control of boll weevil (*Anthonomus grandis*) the test unit consisted of 24-well-microtiter plates containing an insect diet and 20-30 *A. grandis* eggs.

The compounds or mixtures were formulated using a solution containing 75% water and 25% DMSO. Different concentrations of formulated compounds or mixtures were sprayed onto the insect diet at 20 µl, using a custom built micro atomizer, at two replications.

For experimental mixtures in these tests identical volumes of both mixing partners at the desired concentrations respectively, were mixed together.

After application, microtiter plates were incubated at 23+1° C., 50+5% RH for 5 days. Egg and larval mortality was then visually assessed.

In this test the compound I-2 and N-[2-(1,1,2,3,3,3-hexafluoropropoxy)-phenyl]-3-difluoromethyl-1-methyl-1H-pyrazole-4-carboxamide (compound 3.1), and N-(3',4',5'-trifluorobiphenyl-2-yl)-1-methyl-3-difluoromethyl-1H-pyrazole-4-carboxamide (compound 3.2) were used.

Following results were obtained

| Boll Weevil | ppm | Average Control % |
| --- | --- | --- |
| I-2 | 0.5 | 0 |
| 3.1 | 40 | 0 |
| 3.2 | 200 | 50 |
| I-2 + 3.1 | 0.5 + 40 | 100* |
| I-2 + 3.2 | 0.5 + 200 | 100* |

*synergistic control effect according to Colby's equation

Use Example 4

For evaluating control of green peach aphid (*Myzus persicae*) through systemic means the test unit consisted of 96-well-microtiter plates containing liquid artificial diet under an artificial membrane.

The compounds or mixtures were formulated using a solution containing 75% water and 25% DMSO. Different concentrations of formulated compounds or mixtures were pipetted into the aphid diet, using a custom built pipetter, at two replications.

For experimental mixtures in these tests identical volumes of both mixing partners at the desired concentrations respectively, were mixed together.

After application, 5 to 8 adult aphids were placed on the artificial membrane inside the microtiter plate wells. The aphids were then allowed to suck on the treated aphid diet and incubated at 23+1° C., 50+5% RH for 3 days. Aphid mortality and fecundity was then visually assessed. For the mixture tested the results are listed in table 2.

In this test the compound I-2, and 5-chloro-7-(4-methylpiperidin-1-yl)-6-(2,4,6-trifluorophenyl)-[1,2,4]triazolo[1,5-a]pyrimidine (compound 2.2) and N-[2-(1,1,2,3,3,3-hexafluoropropoxy)-phenyl]-3-difluoromethyl-1-methyl-1H-pyrazole-4-carboxamide (compound 3.1) were used.

Following results were obtained

| Green Peach Aphid | ppm | Average Control % |
|---|---|---|
| I-2 | 0.5 | 0 |
| 2.2 | 8 | 0 |
| 3.1 | 1000 | 0 |
| I-2 + 2.2 | 0.5 + 8 | 75* |
| I-2 + 3.1 | 0.5 + 1000 | 100* |

*synergistic control effect according to Colby's equation

The invention claimed is:

1. A pesticidal mixture comprising, as active components:
1) an anthranilamide compound of the formula I

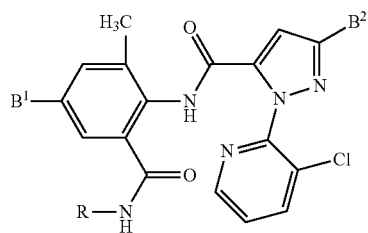

in which the substituents are as defined below:
B¹ is hydrogen, cyano or chlorine;
B² is bromine or CF₃; and
R is hydrogen or $C_1$-$C_6$-alkyl;
and
2) one or more fungicidal compounds II selected from the group consisting of bixafen, 5-chloro-7-(4-methylpiperidin-1-yl)-6-(2,4,6-trifluorophenyl)-[1,2,4]triazolo[1,5-a]pyrimidine, and N-[2-(1,1,2,3,3,3-hexafluoropropoxy)-phenyl]-3-difluoromethyl-1-methyl-1H-pyrazole-4-carboxamide,
in a synergistically effective amount.

2. The pesticidal mixture of claim 1, comprising the compound of formula I and the compound II in a weight ratio of from 100:1 to 1:100.

3. The pesticidal mixture of claim 1, wherein the compound of formula I is 3-bromo-4'-cyano-1-(3-chloro-2-pyridyl)-2'-methyl-6'-(methylcarbamoyl)pyrazole-5-carboxanilide.

4. The pesticidal mixture of claim 1, wherein the compound of formula I is 3-bromo-4'-chloro-1-(3-chloro-2-pyridyl)-2'-methyl-6'-(methylcarbamoyl)pyrazole-5-carboxanilide.

5. The pesticidal mixture of claim 1, comprising two fungicidal compounds II and the compound of formula I.

6. A pesticidal composition, comprising a liquid or solid carrier and the mixture of claim 1.

7. A method for controlling phytopathogenic harmful fungi, wherein the fungi, their habitat or the plants to be protected against fungal attack, the soil or seed are treated with an effective amount the mixture of claim 1.

8. A method for controlling insects, arachnids or nematodes comprising contacting an insect, acarid or nematode or their food supply, habitat, breeding grounds or their locus with the mixture of claim 1 in pesticidally effective amounts.

9. A method for protecting plants from attack or infestation by insects, acarids or nematodes comprising contacting the plant, or the soil or water in which the plant is growing, with the mixture of claim 1 in pesticidally effective amounts.

10. The method of claim 8, wherein the mixture is applied in an amount of from 5 g/ha to 2000 g/ha.

11. A method for protection of seed comprising contacting the seeds with the mixture of claim 1 in pesticidally effective amounts.

12. The method of claim 11 wherein the mixture is applied in an amount of from 0.001 g to 10 kg per 100 kg of seeds.

13. Seed, comprising the mixture of claim 1 in an amount of from 0.1 g to 10 kg per 100 kg of seeds.

14. A method for controlling phytopathogenic harmful fungi, wherein the fungi, their habitat or the plants to be protected against fungal attack, the soil or seed are treated with an effective amount of
1) an anthranilamide compound of the formula I

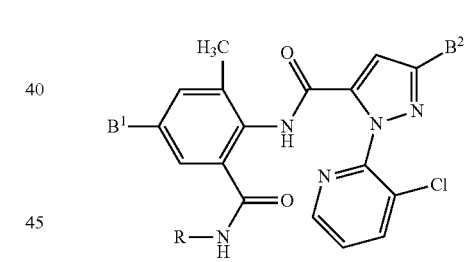

in which the substituents are as defined below:
B¹ is hydrogen, cyano or chlorine;
B² is bromine or CF₃; and
R is hydrogen or $C_1$-$C_6$-alkyl;
and
2) one or more fungicidal compounds II selected from the group consisting of bixafen, 5-chloro-7-(4-methylpiperidin-1-yl)-6-(2,4,6-trifluorophenyl)-[1,2,4]triazolo[1,5-a]pyrimidine, and N-[2-(1,1,2,3,3,3-hexafluoropropoxy)-phenyl]-3-difluoromethyl-1-methyl-1H-pyrazole-4-carboxamide, and
wherein the compound of formula I and the compound II are applied simultaneously, separately, or in succession.

* * * * *